United States Patent
Scher et al.

[11] Patent Number: 6,015,571
[45] Date of Patent: Jan. 18, 2000

[54] MICROCAPSULES CONTAINING SUSPENSIONS OF BIOLOGICALLY ACTIVE COMPOUNDS

[75] Inventors: Herbert B. Scher, Moraga; Jin Ling Chen, El Cerrito, both of Calif.

[73] Assignee: Zeneca Limited, United Kingdom

[21] Appl. No.: 08/354,409

[22] Filed: Dec. 12, 1994

Related U.S. Application Data

[63] Continuation of application No. 08/153,111, Nov. 15, 1993, abandoned.

[51] Int. Cl.$^7$ ..................................................... A01N 25/28
[52] U.S. Cl. ........................ 424/408; 424/417; 424/419; 424/405; 424/484; 424/489; 424/501; 504/112; 504/118; 428/402.24; 264/4.1; 264/4.7; 264/5
[58] Field of Search ................................ 264/4.1, 4.7, 5; 424/405, 489, 501, 408, 417, 419; 428/402.24; 504/112, 118

[56] References Cited

U.S. PATENT DOCUMENTS

| | | |
|---|---|---|
| 2,800,458 | 7/1957 | Green . |
| 4,140,516 | 2/1979 | Scher .......................................... 71/88 |
| 4,285,720 | 8/1981 | Scher . |
| 4,557,755 | 12/1985 | Takahashi et al. ........................ 71/100 |
| 4,722,838 | 2/1988 | Tocker . |
| 4,938,797 | 7/1990 | Hasslin et al. ............................. 71/118 |
| 5,160,529 | 11/1992 | Scher et al. ............................... 71/118 |
| 5,418,010 | 5/1995 | Janda et al. ......................... 427/213.31 |
| 5,470,512 | 11/1995 | Noji et al. ................................. 264/4.1 |
| 5,674,519 | 10/1997 | Curtis et al. ............................. 424/408 |

FOREIGN PATENT DOCUMENTS

| | | |
|---|---|---|
| 252897 | 1/1988 | European Pat. Off. . |
| 270742 | 6/1988 | European Pat. Off. . |
| 281521 | 9/1988 | European Pat. Off. . |
| 929402 | 6/1963 | United Kingdom . |
| 2011341 | 7/1979 | United Kingdom . |
| 92/10285 | 6/1992 | WIPO . |

*Primary Examiner*—Neil S. Levy
*Attorney, Agent, or Firm*—David P. LeCroy

[57] ABSTRACT

Microcapsules containing a suspension of a soild, biologically active compound in an organic, water-immiscible liquid and processes for their preparation.

27 Claims, No Drawings

MICROCAPSULES CONTAINING SUSPENSIONS OF BIOLOGICALLY ACTIVE COMPOUNDS

This application is a continuation of application Ser. No. 08/153,111, filed Nov. 15, 1993 now abandoned.

FIELD OF THE INVENTION

This invention relates to microencapsules which contain a solid biologically active compound suspended in a liquid, and processes for their preparation and for the use of such microcapsules.

BACKGROUND AND PRIOR ART

Microcapsule technology has been in existence for a number of years. Microcapsules have a variety of uses, especially for containing dyes, inks, chemical reagents, pharmaceuticals, flavoring materials, and more especially agrochemicals, that is fungicides, bactericides, insecticides, herbicides and the like.

The development and uses of microencapsulation are described by Gordon Marrs and Herbert B. Scher in Chapter 4 of "Controlled Delivery of Crop Protection Agents" (London, Taylor and Francis, 1990). As discussed by Marrs and Scher, there are three methods of forming microcapsules: i) physical methods, ii) phase separation methods and iii) interfacial polymerization.

In the third of these methods, the walls of microcapsules are generally formed of polymeric material produced by a polymerization reaction which preferably takes place at the interface between two phases, usually an aqueous phase and a water-immiscible organic phase. Thus, they may be produced from a water-in-oil emulsion or more usually an oil-in-water emulsion.

A basic patent dealing with microcapsule technology is U.S. Pat. No. 4,285,720. In this patent the walls of the microcapsules are produced from polymers formed by reactions of isocyanate monomers.

A second means of forming microcapsules by interfacial polymerization is described in U.S. Pat. No. 4,956,129. In this patent polymeric microcapsule walls are produced from etherified urea-formaldehyde prepolymers which undergo self-condensation polymerization under acid conditions.

Various improvements on these techniques have been suggested. For example, U.S. Pat. No. 4,140,516, describes the use of phase transfer catalysts while U.S. Pat. No. 4,448,929, describes the use of an improved protective colloid. However, in all these patents, the process have been applied only to liquids, i.e., to materials which are liquid at ambient temperature or to solutions. Unfortunately, many biologically active compounds are solids with high melting points and are not readily soluble in most commonly used solvents. The benefits of microencapsulation e.g., controlled release and increased longevity of efficacy have not been readily available to such compounds using known techniques.

It is also known to surround solids by a polymer matrix. Thus, in U.S. Pat. No. 4,428,983, there is described a process for producing quartz crystals in a polymer matrix. The patent uses the term suspension for describing the paste of quartz crystals in the prepolymer, but this publication does not describe the production of microcapsules containing a solid suspended in a liquid.

There are a large number of publications dealing with the production and application of microencapsulated formulations of haloacetanilide herbicides. These include U.S. Pat. No. 4,280,833; 4,417,916; 4,534,783; 4,563,212; and 4,640,709. Additionally, U.S. Pat. No. 4,936,901 discloses herbicidal compositions which are dry flowable water-dispersible granular formulations comprising a mixture of microcapsules of a water-insoluble pesticide (including a haloacetanilide herbicide) encapsulated within a polymeric shell wall and at least one other pesticide which is nonencapsulated. Such compositions were necessary since no satisfactory techniques to produce a microcapsule containing a solid, biologically activate herbicide suspended in a liquid have been known.

It is not surprising that capsules containing a biologically active solid suspended in a liquid have not been made up until the present time since the problems to be faced in producing such a capsule are formidable. For example, in forming such capsules from an oil-in-water emulsion, the following difficulties must be addressed:

Firstly, a stable suspension of the solid in a water-immiscible liquid must be produced. If dispersants or surfactants are used, they must not interfere with further processes of dispersion used in making microcapsules.

Secondly, the suspension must be dispersed in water to produce stable, well dispersed droplets. For biologically active substances, it is preferable to have very small droplets of liquid dispersed in water to present a high surface area in the resulting microcapsules. To produce very small droplets requires high shear forces which would tend to break down the droplets and/or release the solid from suspension. Surfactants are usually required to achieve good dispersion and stable droplets.

Thirdly, the presence of one or more surfactants can make the dispersed droplet system unstable and the phenomenon of phase inversion may occur i.e., the water forms small droplets within the liquid, a water-in-oil emulsion.

Fourthly, the solid suspended in the water-immiscible liquid is liable to migrate to the aqueous phase, particularly when emulsifying surfactants are used.

SUMMARY OF THE INVENTION

It has now been found that the above problems can be overcome and it is possible to produce microcapsulated compositions containing a solid biologically active compound suspended in a liquid.

DETAILED DESCRIPTION OF THE INVENTION

In accordance with the invention, a microencapsulated formulation of a solid biologically active compound suspended in a liquid is produced by phase separation or interfacial polymerization techniques. The preferred technique is interfacial polymerization, especially producing the capsules from an oil-in-water emulsion by procedures such as those described in U.S. Pat. No. 4,285,720, and U.S. Pat. No. 4,956,129, modified as described herein.

The solid, biologically active compound is preferably an agrochemical and especially a herbicide.

Preferred herbicides are s-triazines, e.g., atrazine, simazine, propazine, cyprozine;

Sulphonylureas e.g., chlorsulfuron, chlorimuronethyl, metsulfuron-methyl, thiameturon-methyl; and Triketones e.g., sulcotrione.

An especially preferred herbicide is atrazine.

Another suitable compound is the fungicide (E)methyl-2-[2-(6-(2-cyanophenoxy)pyrimidin-4-yloxy)phenyl]-3-methoxypropenoate.

The liquid in which the solid is suspended may suitably be a second herbicide, especially a thiocarbamate or a haloacetanilide and preferably acetochlor.

The haloacetanilides, particularly the subclass generally known as α-chloroacetanilides, are a well-known class of herbicidal agents and have been used and proposed for use in a number of crop and non-crop applications. Some of the better known members of this class include α-chloro-6'-ethyl-N-(2-methoxy-1-methylethyl)-acetanilide (metolachlor), N-butoxymethyl-α-chloro-2',6'-diethylacetanilide (butachlor), α-chloro-2',6'-diethyl-N-methoxymethylacetanilide (alachlor), 2-chloro-N-(ethoxymethyl)-6'-ethyl-o-acetotoluidide (acetochlor) and α-chloro-N-isopropylacetanilide (propachlor). Many other compounds of this type are disclosed in numerous patents.

The thiocarbamates are a well known class of herbicide which includes

Molinate - S-ethyl hexahydro-1H-azepine-1-carbothioate
Butylate - S-ethyl diisobutylthiocarbamate
EPTC - ethyl dipropylthiolcarbamate
Triallate - 2,3,3-trichloroallyl-diisopropylthiolcarbamate
Diallate - cis-1-trans-2,3-dichloroallyl-diisopropylthiolcarbamate
Vernolate - S-propyl dipropylthiolcarbamate When the liquid is a herbicide, the microcapsules of the invention suitably contain 0.1–55% by weight of biologically active compounds.

The liquid may alternatively be any organic solvent which is immiscible with water, does not dissolve the biologically active solid to appreciable extent and is polar enough to dissolve the prepolymers used to form the walls of the microcapsules.

Suitable examples of such solvents are aromatic compounds such as xylenes or naphthalenes, especially Solvesso 200; aliphatic compound such as alkyl esters, especially alkyl acetates, e.g., Exxate 700—Exxate 1000; alkyl phthalates, such as diethyl phthalate, dibutylphthalate; alcohols, such as isopropyl alcohol; ketones, such as acetophenone, cyclohexanone. The solvent may be a mixture of more than are compound.

A safener for either herbicide may be present and many such safeners or antidotes as well known in the art. Preferred types for use with haloacetanilide herbicides include dichloroacetamides such as dichlormid (N,N-diallyl dichloroacetamide);2,2,5-trimethyl-3-dichloroacetyl oxazolidine (R-29148),N-dichloroacetyl-1-oxa-4-azaspiro[4,5]decane (AD-67);4-dichloroacetyl-2,3-dihydro-3-methyl-1,4-benzoxazine (CGA-154281);1-(dichloroacetyl)hexahydro-3,3,8a-trimethylpyrrolo-[1,2-a]-pyrimidin-6 (2H)-one and N-(1,3-dioxolan-2-yl-methyl)-N-(2-propenyl)-2,2-dichloroacetamide (PPG-1292).

These and other dichloroacetamides are described, for instance, in U.S. Pat. Nos. 4,124,372; 4,256,481; 4,294,764; 4,448,960; 4,601,745; 4,618,361; 4,708,735 and 4,900,350. Additional known types of safeners or antidotes include certain oxime derivatives (U.S. Pat. Nos. 4,070,389 and 4,269,775, for instance), thiazole carboxylic acids and derivatives (U.S. Pat. No. 4,199,506 for instance), haloacyltetrahydroisoquinolines (U.S. Pat. No. 4,755,218, for example), aryl cyclopropane carbonitriles (U.S. Pat. No. 4,859,232, for example) and 1,8-naphthalic acid, its anhydride and derivatives.

Safeners or antidotes, when included, will usually be contained in the organic or water-immiscible phase.

The preferred materials for the microcapsule is a polyurea, formed as described in U.S. Pat. No. 4,285,720, or a urea-formaldehyde polymer as described in U.S. Pat. No. 4,956,129. The polyurea is especially preferred.

In brief, the process comprises the following steps.

Step 1. Producing the solid biologically active material with the required particle size, suitably by a milling process. The preferred average particle size of the solid is 0.01–50 microns, preferably 1–10 microns and even more preferably 1–5 microns.

Step 2. Suspending the solid biologically active material in an organic liquid. The liquid is preferably a poor solvent for the solid, that is it will not dissolve large quantities of the solid. The liquid must also be immiscible with water, but polar enough to dissolve the prepolymers used in the microencapsulation process.

The liquid preferably contains a dispersant capable of keeping the solid in the liquid but which does not allow the solid to be extracted into the water when the suspension is dispersed into water. In addition, when the suspension is added to water, the dispersant must not allow phase inversion to occur i.e., the water must not be allowed to be taken into an emulsion by the organic liquid.

The exact choice of dispersants will depend on the choice of solid and the liquid but preferred dispersants are non-ionic surfactants which act by steric hindrance and are active only at the solid/organic liquid interface and do not act as emulsifying agents. Such dispersants are suitably made up of i) a polymeric chain having a strong affinity for the liquid and ii) a group which will absorb strongly to the solid.

Examples of such dispersants include phthalocyanine derivatives, polyoxyalklene amine derivatives, polyamine polymers, polyester polymers, various derivatives of polycondensed fatty acids, including metal derivatives, amine derivatives and ammonium derivatives, all available under the tradenames Hypermer and Atlox from ICI Americas Inc., Wilmington, Del., e.g., Atlox LP1, Atlox LP2, Atlox LP3, Atlox LP4, Atlox LP5, Atlox LP6, Atlox PS2, Atlox PS3, Hypermer PS1, Hypermer PS2, Hypermer PS3, and Hypermer LP2; and vinylpyrrolidone polymers available under the tradename Agrimer AL from GAF such as Agrimer AL-220 and Agrimer AL-216.

In general, the range of dispersant concentration used is from about 0.01 to about 10% by weight based on the organic phase, but higher concentration of surfactant may also be used.

Alternatively, the procedures of Steps 1 and 2 may be varied by preforming a milling process, to reduce the particle size of the solid, after the solid biologically active material is suspended in the organic liquid (media milling).

Step 3. A physical dispersion of a water-immiscible phase in an aqueous phase is prepared. To obtain the appropriate dispersion, the organic phase is added to the aqueous phase, with stirring. A suitable dispersing means is employed to disperse the organic phase in the liquid phase. The means may be any high shear device, so as to obtain a desired droplet (and corresponding microcapsule particle) size within the range of from about 1 to about 200 microns. Preferably the droplet size is from about 1 to about 30 microns, most preferably from about 3 to about 20 microns, average. Once the proper droplet size is obtained, the dispersion means is discontinued. Only mild agitation is required for the remainder of the process. The water-immiscible phase comprises the solid, biologically active compound suspended in the liquid to be encapsulated prepared as described above in Steps 1 and 2. The aqueous phase is comprised of water and a material termed a "protective colloid". Preferably it further contains a surfactant.

In general, the surfactant or surfactants in this phase may be anionic or non-ionic surfactants with an HLB range of from about 12 to about 16 that is high enough to form a stable oil-in-water emulsion. If more than one surfactant is used, the individual surfactants may have values lower than 12 or higher than 16. However, when combined together the overall HLB value of the surfactants will be in the range 12–16. Suitable surfactants include polyethylene glycol ethers of linear alcohols, ethoxylated nonylphenols, naphthalene sulfonates, and the like. Other suitable surfactants include block copolymers of propylene oxide and ethylene oxide and anionic/nonionic blends. Preferably the hydrophobic portion of the surfactant has chemical characteristics similar to the organic liquid. Thus, when the organic liquid is an aromatic solvent, the surfactant would suitably be an ethoxylated nonphylphenol.

Especially preferred surfactants are Tergitol NP7, Tergitol NP40 and Tergitol 15-S-20.

In general, the range of surfactant concentration in the process is from about 0.01 to about 10.0 percent by weight, based on the aqueous phase, but higher concentrations of factant may also be used.

The protective colloid present in the aqueous (or continuous) phase must absorb strongly onto the surface of the oil droplets. Suitable colloid forming materials include one or more of polyalkylates, methyl cellulose, polyvinyl alcohol, polyacrylamide, poly(methylvinyl ether/maleic anhydride), graft copolymers of polyvinyl alcohol and methylvinyl ether/maleic acid (hydrolyzed methylvinyl ether/maleic anhydride; see U.S. Pat. No. 4,448,929, which is hereby incorporated by reference herein), and alkali metal or alkaline earth metal lignosulfonates. Preferably, however, the protective colloid is selected from alkali metal and alkaline earth metal lignosulfonates, most preferably sodium lignosulfonates. Especially preferred colloids also contain polyvinyl alcohol.

There must be sufficient colloid present to afford complete coverage of the surfaces of all the droplets of the organic liquid. The amount of protective colloid employed will depend on various factors, such as molecular weight, compatibility, etc. The protective colloid can be added to the aqueous phase prior to the addition of the organic phase, or can be added to the overall system after the addition of the organic phase or the dispersion of it. The protective colloid is generally present in the aqueous phase in an amount of from about 0.1 to about 10.0 percent by weight.

Any surfactant used in the aqueous phase must not displace the protective colloid from the surface of the droplets of organic liquid.

If the water-immiscible liquid is a thiocarbamate or a haloacetanilide herbicide, then depending on the intended application or use of this microencapsulated product, the compositions of this invention may also include a herbicide safener or antidote.

Safeners or antidotes, when included, will usually be contained in the organic or water-immiscible phase.

The preferred average particle size of the droplets of the water-immiscible liquid containing a biologically active solid in 1–200 microns, preferably 1–30 microns and more preferably 3–20 microns. Particle size can be adjusted according to the end use of the microcapsules by adjusting stirring speed and time, and by the choice of surfactants and the amount of surfactants employed.

In order to obtain the microcapsules, the organic liquid and/or the water must contain one or more materials which can react to form a polymer at the interface between the organic liquid and the water.

In the process described in U.S. Pat. No. 4,285,720, polyisocyanates are dissolved in the organic phase (i.e., at Step 2 in the above procedure) and polymerization takes place by hydrolysis of the prepolymers at the water/organic liquid interface to form amines which, in turn, react with unhydrolyzed monomers to form the polyurea microcapsule wall. A single compound or a mixture of two or more polyisocyanates may be used. Mixtures are preferred. Of the polyisocyanates, polymethylene polyphenylisocyanate (PAPI), and isomeric mixtures of toluene diisocyanate (TDI) are preferred. Particularly preferred are mixtures of polymethylene polyphenylisocyanate with isomeric mixtures of toluene diisocyanate, in a weight ratio of PAPI:TDI of from about 1:30 to about 4:1, especially 1:10 to 1:1.

The amount of the organic polyisocyanate used in the process will determine the wall content of the microcapsules formed. In general, the polyisocyanate (or microcapsule wall formed from it) will comprise from about 2.0 to about 75.0 percent by weight of the microcapsule. Most preferably the wall will comprise from about 4 to about 15% by weight, of the microcapsule.

The dispersion is maintained in a temperature range of from about 20° C. to about 90° C. preferably 40°–60° C. during which the condensation reaction takes place to form the polyurea, at the interfaces between the droplets of the organic phase and the aqueous phase.

A thiocarbamate or a haloacetanilide herbicide may be used as a solvent for the polyisocyanates. Alternatively, solvents such as xylene may be used (see Canadian Patent 1,094,402).

Another suitable system for forming microcapsules is described in U.S. Pat. No. 4,956,129, in which the polymer is formed from an etherified urea-formaldehyde prepolymer in which 50–98% of the methylol groups have been etherified with a $C_4$–$C_{10}$ alcohol. Self-condensation of the prepolymer takes place under the action of heat at low pH.

To form the microcapsules, the temperature of the two-phase mixture is raised to a value of from about 20° C. to about 90° C., preferably from about 40° C. to about 90° C., most preferably from about 40° C. to about 60° C. Depending on the system, the pH value may be adjusted to an appropriate level.

The following are examples of preparations of compositions of this invention.

GENERAL PROCEDURE

In the first two examples which follow, the compositions were prepared by the following general procedure:

The organic phase was added to the aqueous phase, and an oil-in-water emulsion was formed by means of a high shear stirrer. The average particle size was in the range of 11.0±2 microns. While mild agitation was maintained, the temperature of the batch was raised to 50° C. over a period of 30 minutes, and held at 50° C. for 3 hours. The resulting microcapsule suspension was then allowed to cool to room temperature. The additional ingredients were then added and the pH was then adjusted to 11.0 with 50% caustic.

In the third example, the pH of the aqueous phase was adjusted to 2.0. Then the organic phase was added to the aqueous phase, and an oil-in-water emulsion was formed by means of high shear stirrer. The average particle size was in the range of 28±3 microns. While mild agitation was maintained, the temperature of the batch was raised to 50° C. over a period of 30 minutes and held at 50° C. for 3 hours. The resulting microcapsule suspension was then allowed to cool to room temperature. The additional ingredients were then added and the pH was adjusted to 7.0 with 50% caustic.

EXAMPLE I 14473-27-1

A composition was prepared using the general procedure described above with the following ingredients.

| Component | Weight, g. | Weight % |
|---|---|---|
| ORGANIC PHASE | | |
| Atrazine (technical grade) | 65.0 | 16.58 |
| Acetochlor (technical grade) | 100.0 | 25.51 |
| N,N-diallyldichloroacetamide | 17.0 | 4.33 |
| Hypermer LP5 | 9.0 | 2.30 |
| Hypermer LP1 | 4.0 | 1.02 |
| Polymethylene polyphenylisocyanate | 2.0 | 0.51 |
| Toluene diisocyanate | 9.0 | 2.29 |
| AQUEOUS PHASE | | |
| Reax 100M (sodium salt of ligno-sulfonic acid, 40% solution in water) | 18.0 | 4.59 |
| Gelvatol 40/10 (PVA, 20% solution in water) | 18.0 | 4.59 |
| Tergitol NP7 (20% solution in water) | 4.0 | 1.02 |
| Tergitol NP40 (70% solution in water) | 1.0 | 0.26 |
| Water | 138.8 | 35.15 |
| ADDITIONAL INGREDIENTS | | |
| Attapulgite (attagel 40)[1] | 3.8 | 0.98 |
| Xanthan gum (Kelzan)[1] | 0.3 | 0.07 |
| Sodium carbonate[2] | 2.7 | 0.70 |
| Proxel GXL[3] | 0.4 | 0.10 |
| TOTAL | 393.0 | 100.00 |

The resulting microencapsulated product had an average particle diameter of 10.0 microns.

[1]=suspending agent
[2]=buffering agent
[3]=biocide

EXAMPLE II 14585-26

A composition was prepared using the general procedure described above with the following ingredients.

| Component | Weight, g. | Weight % |
|---|---|---|
| ORGANIC PHASE | | |
| 2-(2-nitro-4-methanesulfonyl-benzoyl)-1,3-cyclohexanedione | 50.0 | 12.50 |
| Solvesso 200 | 115.0 | 28.75 |
| Hypermer LP6 (40% solution in hydrocarbons) | 32.0 | 8.00 |
| Polymethylene polyphenylisocyanate | 8.0 | 2.00 |
| Toluene diisocyanate | 8.0 | 2.00 |
| AQUEOUS PHASE | | |
| Reax 100M (sodium of lignosulfonic acid, 40% solution in water) | 18.0 | 4.50 |
| Gelvatol 40/10 (PVA, 20% solution in water) | 18.0 | 4.50 |
| Tergitol NP7 (20% solution in water) | 4.0 | 1.00 |
| Tergitol NP40 (70% solution in water) | 1.0 | 0.25 |
| Water | 138.8 | 34.70 |
| ADDITIONAL INGREDIENTS | | |
| Attapulgite (attagel 40) | 3.8 | 0.95 |
| Xanthan gum (Kelzan) | 0.3 | 0.07 |
| Sodium carbonate | 2.7 | 0.68 |
| Proxel GXL | 0.4 | 0.10 |
| TOTAL | 400.0 | 100.00 |

The resulting microencapsulated product had an average particle diameter of 12.5 microns.

EXAMPLE III 14369-21-3

A composition was prepared using the general procedure described above with the following ingredients.

| Component | Weight, g. | Weight % |
|---|---|---|
| ORGANIC PHASE | | |
| Atrazine (technical grade) | 39.8 | 10.00 |
| Solvesso 200 | 92.7 | 23.28 |
| Beetle 1050 Resin (butylated urea-formaldehyde prepolymer, 60% solution in butanol) | 26.6 | 6.68 |
| AQUEOUS PHASE | | |
| Petro BAF (sodium dialkylnaphthalen-sulfonate) | 0.8 | 0.20 |
| Reax 100M (sodium salt of ligno-sulfonic acid, 40% solution in water) | 18.8 | 4.72 |
| Water | 215.0 | 53.99 |
| ADDITIONAL INGREDIENTS | | |
| Attapulgite (attagel 40) | 3.8 | 0.95 |
| Xanthan gum (Kelzan) | 0.3 | 0.08 |
| Proxel GXL | 0.4 | 0.10 |
| TOTAL | 398.2 | 100.00 |

The resulting microencapsulated product had an average particle diameter of 28 microns.

In each Example the final product of the process was analyzed by microscopy and polarography. The results showed that the suspension of biologically active solid was successfully microencapsulated and the aqueous phase was substantially free of the solid.

What is claimed is:

1. A microcapsule containing a solid agrochemical material suspended in a water-immiscible organic liquid and from about 0.01 to about 10 percent by weight, based on the weight of the capsule and its contents, of a dispersant which functions to keep the solid in the liquid but does not allow the solid to be extracted into water, is active only at the solid/organic liquid interface and does not act as an emulsifying agent, said microcapsule having an average particle size of about 1–200 microns, wherein said solid has an average particle size of about 0.01–50 microns, and wherein said solid is an herbicide.

2. A microcapsule according to claim 1 in which the dispersant molecule comprises a polymeric chain having a strong affinity for the organic liquid and a group which will absorb strongly to the agrochemical material.

3. A microcapsule according to claim 1 in which the agrochemical material is a compound.

4. A microcapsule according to claim 1 wherein the herbicide is atrazine.

5. A microcapsule according to claim 1 wherein the liquid is an agrochemical material.

6. A microcapsule according to claim 5 wherein the liquid is a herbicide.

7. A microcapsule according to claim 6 wherein the liquid herbicide is a haloacetanilide or a thiocarbamate.

8. A microcapsule according to claim 7 wherein the liquid herbicide is acetochlor.

9. A microcapsule according to claim 6 wherein a herbicide safener is also present in the microcapsule.

10. A microcapsule according to claim 9 wherein the safener is in the liquid herbicide.

11. A microcapsule according to claim 10 wherein the safener is a dichloroacetamide.

12. A microcapsule formed of polyurea or urea-formaldehyde polymer according to claim 1.

13. A polyurea microcapsule according to claim 12 in which the polyurea is formed by polymerizing a mixture of polymethylene polyphenyl isocyanate and an isomeric mixture of toluene diisocyanate.

14. A microcapsule according to claim 13 in which the weight ratio of polymethylene polyphenylisocyanate to mixtures of toluene diisocyanate is from about 1:30 to about 4:1.

15. A microcapsule according to claim 13 in which the weight ratio of polymethylene polyphenylisocyanate to mixtures of toluene diisocyanate is from about 1:10 to about 1:1.

16. A microcapsule according to claim 12 in which the polyurea comprises from about 4 to about 15% by weight of the capsule.

17. A microcapsule according to claim 13 in which the polyurea comprises from about 4 to about 15% by weight of the capsule.

18. A microcapsule according to claim 1 having an average particle size of about 1–30 microns.

19. A microcapsule according to claim 12 having an average particle size of about 3–20 microns.

20. A microcapsule according to claim 1 containing from about 0.1 to about 55 weight percent of agrochemical material.

21. A microcapsule according to claim 12 containing from about 0.1 to about 55 weight percent of agrochemical material.

22. A microcapsule according to claim 1 in which the capsule is formed from a urea-formaldehyde prepolymer.

23. A microcapsule according to claim 22 in which the urea-formaldehyde polymer is produced from an etherified urea-formaldehyde prepolymer in which from about 50% to about 98% of the methylol groups of the said prepolymer have been etherified with a $C_4$–$C_{10}$ alcohol.

24. A microcapsule according to claim 23 in which about 70% to 90% of the methylol groups of the prepolymer have been etherified with a $C_4$–$C_6$ alcohol.

25. A microcapsule according to claim 22 in which the polymer comprises from about 4 to about 15% by weight of the capsule.

26. A microcapsule according to claim 23 in which the polymer comprises from about 4 to about 15% by weight of the capsule.

27. A microcapsule according to claim 24 in which the polymer comprises from about 4 to about 15% by weight of the capsule.

* * * * *